(12) United States Patent
Richter et al.

(10) Patent No.: US 7,033,386 B2
(45) Date of Patent: Apr. 25, 2006

(54) STENT

(75) Inventors: Jacob Richter, Ramat Hasharon (IL); Gregory Pinchasik, Herzlia (IL)

(73) Assignee: Medinol Ltd., Tel Aviv (IL)

( * ) Notice: Subject to any disclaimer, the term of this patent is extended or adjusted under 35 U.S.C. 154(b) by 0 days.

(21) Appl. No.: 10/618,182

(22) Filed: Jul. 11, 2003

(65) Prior Publication Data

US 2004/0098102 A1 May 20, 2004

Related U.S. Application Data

(63) Continuation of application No. 09/519,163, filed on Mar. 6, 2000, now Pat. No. 6,666,881, which is a continuation of application No. 09/361,704, filed on Jul. 27, 1999, now abandoned, which is a continuation of application No. 08/679,606, filed on Jul. 11, 1996, now abandoned, which is a continuation of application No. 08/297,275, filed on Aug. 26, 1994, now abandoned, which is a continuation of application No. 08/029,493, filed on Mar. 11, 1993, now abandoned.

(51) Int. Cl.
*A61F 2/06* (2006.01)

(52) U.S. Cl. .................. 623/1.19; 623/1.18; 236/1 C

(58) Field of Classification Search ............... 623/1.11, 623/1.12, 1.18, 1.19, 1.1, 1.15, 1.23, 11.11, 623/900, 1.2, 902, 903; 606/27–31, 38, 41–50, 606/108, 1, 191–200
See application file for complete search history.

(56) References Cited

U.S. PATENT DOCUMENTS 3,058,705 A    10/1962  Hagg et al.
3,868,956 A    3/1975  Alfidi et al.
4,130,904 A    12/1978  Whalen
4,359,626 A *  11/1982  Potter .......................... 219/490
4,503,569 A    3/1985  Dotter
4,665,906 A    5/1987  Jervis
4,695,709 A *  9/1987  Sachs et al. ................ 219/494

(Continued)

FOREIGN PATENT DOCUMENTS

BR       P1 9102521       10/1991

(Continued)

OTHER PUBLICATIONS

Nakamura et al., ASAIO Transaction, "Novel Airway Stent Using a Thermal Shape-Memory Ti-Ni Alloy", pp. M319-M321, Jul./Sep. 1991.

*Primary Examiner*—Glenn K. Dawson
(74) *Attorney, Agent, or Firm*—Kenyon & Kenyon LLP

(57) ABSTRACT

A stent and a method of making it from a wire, which method includes winding the wire on a mandrel, heating to form a coiled spring, and reversing the winding direction of the coiled spring to form the reversed coiled spring stent. The stent so formed may be reheated over a special mandrel so as to partly relax the outer portion of some or all of the stent coils. The stent may be made up of two or more sections, with adjoining section wound in opposite senses. Such a stent may be deployed by winding the stent onto a catheter, immobilizing the two ends of the wire and one or more intermediate points, bringing the stent to the location where it is to be deployed, and releasing first the intermediate point or points and then the end points. The release of the wire may be accomplished by heating the thread immobilizing the wire so that the thread breaks and releases the wire.

25 Claims, 13 Drawing Sheets

U.S. PATENT DOCUMENTS

| | | | |
|---|---|---|---|
| 4,788,417 A * | 11/1988 | Graflind | 219/528 |
| 4,795,458 A | 1/1989 | Regan | |
| 4,800,882 A | 1/1989 | Gianturco | |
| 4,820,298 A | 4/1989 | Leveen et al. | |
| 4,829,767 A | 5/1989 | Mecca | |
| 4,878,906 A | 11/1989 | Lindemann et al. | |
| 4,913,141 A | 4/1990 | Hillstead | |
| 4,927,413 A | 5/1990 | Hess | |
| 4,969,458 A | 11/1990 | Wiktor | |
| 5,019,085 A | 5/1991 | Hillstead | |
| 5,037,427 A | 8/1991 | Harada et al. | |
| 5,041,126 A | 8/1991 | Gianturco | |
| 5,067,957 A | 11/1991 | Jervis | |
| 5,089,005 A | 2/1992 | Harada | |
| 5,147,370 A | 9/1992 | McNamara et al. | |
| 5,151,105 A | 9/1992 | Kwan-gett | |
| 5,282,823 A | 2/1994 | Schwartz et al. | |
| 5,342,387 A | 8/1994 | Summers | |
| 5,372,600 A | 12/1994 | Beyar et al. | |
| 5,383,928 A | 1/1995 | Scott et al. | |
| 5,409,470 A | 4/1995 | McIntyre et al. | |
| 5,441,516 A | 8/1995 | Wang et al. | |
| 5,476,505 A | 12/1995 | Limon | |
| 5,522,882 A | 6/1996 | Gaterud et al. | |
| 5,562,641 A | 10/1996 | Flumenblit et al. | |
| 5,725,572 A | 3/1998 | Lam et al. | |
| 5,824,045 A | 10/1998 | Alt | |
| 5,922,020 A | 7/1999 | Klein et al. | |
| 6,013,085 A | 1/2000 | Howard | |
| 6,514,285 B1 | 2/2003 | Pinchasik | |

FOREIGN PATENT DOCUMENTS

| | | |
|---|---|---|
| BR | P1 9202079 | 5/1992 |
| EP | 0 282 175 | 2/1988 |
| EP | 0 282 175 | 9/1988 |
| EP | 0 362 444 | 4/1990 |
| EP | 0 518 704 | 12/1992 |
| EP | 1 101 455 A2 | 5/2001 |
| FR | 2 617 721 | 8/1988 |
| FR | 2 671 482 | 7/1992 |
| GB | 1 540 432 | 2/1979 |
| JP | 1-230375 | 9/1989 |
| JP | 2-207935 | 8/1990 |
| JP | 4-47417 | 2/1992 |
| JP | 4-47457 | 2/1992 |
| JP | 4-207935 | 7/1992 |
| JP | 63-230158 | 9/1998 |
| SU | 845818 | 7/1981 |
| WO | WO91/16005 | 10/1991 |
| WO | WO 92/22263 | 12/1992 |

* cited by examiner

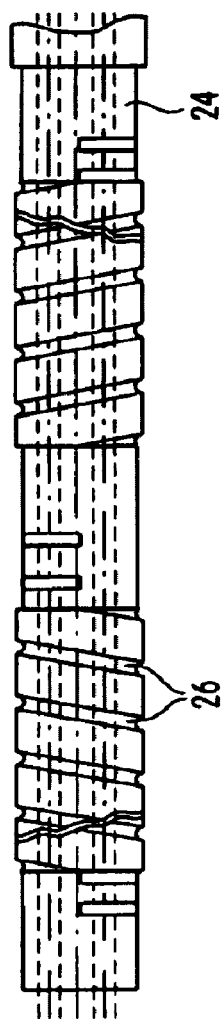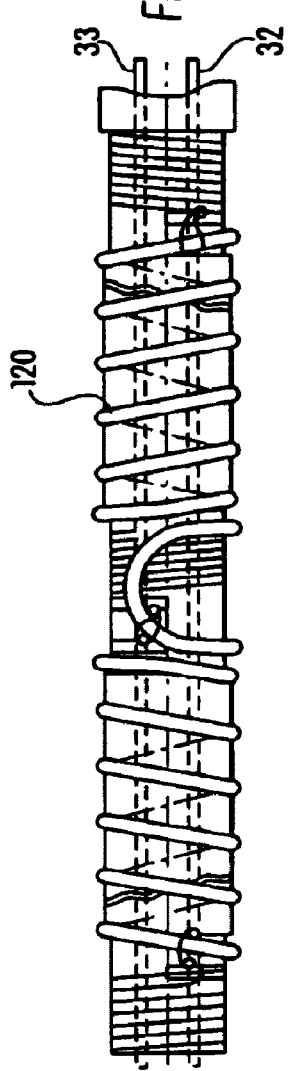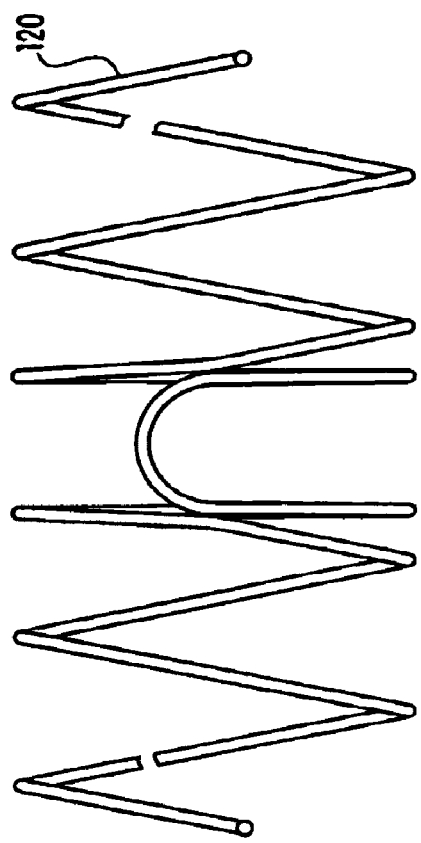

STENT

RELATED PATENT APPLICATIONS

This application is a continuation of prior application No. 09/519,163 filed Mar. 6, 2000, now U.S. Pat. No. 6,666,881, which is a continuation of Ser. No. 09/361,704 filed Jul. 27, 1999, now abandoned, which is a continuation of Ser. No. 08/679,606 filed Jul. 11, 1996, now abandoned, which is a continuation of Ser. No. 08/297,275, filed Aug. 26, 1994 (abandoned), which is a continuation of Ser. No. 08/029,493 filed Mar. 11, 1993 (abandoned).

FIELD AND BACKGROUND OF THE INVENTION

The present invention relates to stents and, more particularly, to methods of fabricating and deploying stents.

The term "stent" has come into widespread use to denote any of a large variety of spring-like support structures, in the form of a tube which is open at both ends, which can be implanted inside a blood vessel or other tubular body conduit, to help keep the vessel or conduit open. Stents may be used following balloon angioplasty to prevent restenosis and may, more generally, be used in repairing any of a number of tubular body conduits, such as those in the vascular, biliary, genitourinary, gastrointestinal and respiratory systems, among others, which have narrowed, weakened, distorted, distended or otherwise deformed, typically as a result of any of a number of pathological conditions.

An effective stent must possess a number of important and very specific characteristics. Specifically, the stent should be chemically and biologically inert to its surroundings and should not react with, or otherwise stimulate, the living tissues around it. The stent must further be such that it will stay in the correct position and continue to support the tubular body conduit into which it is implanted over extended periods of time. Further, the stent must have the ability to return to its prescribed in-place diameter after the stent diameter has been significantly reduced prior to its insertion, usually tightly wrapped on a catheter, into the tubular body conduit.

These requirements limit the suitable metal stent materials to just a few metals and alloys. To date, it has been found that various alloys of nickel and titanium (hereinafter "nitinol"), with or without certain coatings, have the desired properties and are considered suitable for use in stent applications.

Specifically, nitinols, with or without special coatings, have been found to be chemically and biologically inert and to inhibit thrombus formation. Nitinols are, under certain conditions, also superelastic which allows them to withstand extensive deformation and still resume their original shape. Furthermore, nitinols possess shape memory, i.e., the metal "remembers" a specific shape fixed during a particular heat treatment and can resort to that shape under proper conditions. Shape-memory alloys can be formed into a predetermined shape at a suitable heat treatment temperature. At temperatures below the transition temperature range ("TTR") certain nitinol alloys are in their martensite phase wherein they are highly ductile and may be plastically deformed into any of a number of other shapes. The alloy returns to its austenite phase, returning to its original predetermined shape upon reheating to a temperature above the transition temperature range. The transition temperature varies with each specific combination ratio of the components in the alloy.

The superelasticity of nitinols and their shape memory characteristics makes it possible to fabricate a stent having the desired shape and dimensions. Once formed, the stent can be temporarily deformed into a much narrower shape for insertion into the body. Once in place, the stent can be made to resume its desired shape and dimensions. Certain alloys of nickel and titanium can be made which are plastic at temperatures below about 30° C. and are elastic at body temperatures above 35°C. Such alloys are widely used for the production of stents for medical use since these nitinols are able to resume their desired shape at normal body temperature without the need to artificially heat the stent.

While such stents have been proven effective, they continue to suffer from a number of disadvantages. First, there is, in certain cases, a tendency for tissue to grow in the gads between adjoining loops of the stent. Over time, such growth could lead to the constriction, or even the complete closure, of the tubular body conduit in which the stent was introduced in order to keep open. A continuous, gap-free, tube structure with no gaps would eliminate such undesired tissue growth. However, a rigid tube would lack the highly desirable flexibility which a coiled spring configuration offers.

Another disadvantage is that the techniques for locating stents in a body conduit are such that the stents are often installed at a location which is not precisely the intended optimal location.

There is thus a widely recognized need for, and it would be highly advantageous to have, a stent which would be suitably flexible but which would significantly reduce, or even eliminate, the possibility of undesired tissue growth between the coils of the stent.

There is further a widely recognized need for, and it would also be highly advantageous to have, a technique for installing stents which would allow the stent to be located at precisely the desired location, either by controlling the stent design or by devising adequate methods for its accurate release. Furthermore, in those cases where the "shape memory" characteristic is used and the stent is to be heated in its final location in the body to cause it to resume its memorized shape, it is desired and advantageous to have a way of heating the stent which significantly reduces, or even eliminates, the chance of damaging surrounding tissue through heating which is conducted for too long and/or at temperatures which are too high.

SUMMARY OF THE INVENTION

According to the present invention there is provided a method of fabricating a stent from a wire, comprising: (a) winding the wire on a first mandrel; (b) heating the wound wire to form a coiled spring; and (c) after the coiled spring has cooled sufficiently, reversing the winding direction of the coiled spring to form the stent.

Further according to the present invention there is provided a stent comprising a coiled wire characterized in that the wire includes at least one section which is wound in one sense and at least one section which is wound in the opposite sense, deployment of said stent taking place by tightly winding the stent onto a catheter and subsequently allowing the stent to resume its normal dimensions.

Still further according to the present invention there is provided a method of deploying a stent in a desired location, comprising: (a) tightly winding the stent onto a catheter; (b) immobilizing at least two tie-down points on the stent using a disconnectable thread; (c) bringing the stent to the desired location where the stent is to be deployed; (d) causing the thread to disconnect at one or more of the tie-down points, thereby releasing the tie-down point, wherein said disconnectable thread is meltable and said thread is disconnected by heating the thread so as to cause the thread to melt.

Further yet according to the present invention there is provided a method of heating a nitinol stent to cause the stent to shift from its martensite phase to its austenite phase and to monitor the phase change, comprising: (a) electrically connecting the stent to an electrical power supply; (b) supplying electrical current to the stent; (c) sensing a change in at least one electrical property to indicate the phase change; (d) controlling the current in response to the change.

The present invention successfully addresses the shortcomings of the presently known stents and their methods of deployment by providing a stent which is suitably flexible but which is sufficiently tight so as to eliminate the gaps between adjoining windings of the stent, thereby significantly reducing or even eliminating the possibility of undesirable growth of tissue between winding of the stent. The present invention further offers stents and associated deployment techniques which make it possible to accurately install the stent in a specific location of a body tubular conduit.

BRIEF DESCRIPTION OF THE DRAWINGS

The invention is herein described, by way of example only, with reference to the accompanying drawings, wherein:

FIG. 8A is a side view of a catheter such as might be used in FIG. 8;

FIG. 8B is a side view of the catheter of FIG. 8A with the stent wound on the catheter;

FIG. 8C is a side view of the expanded stent after its release;

DESCRIPTION OF THE PREFERRED EMBODIMENTS

The present invention is of improved stents and of methods of making and deploying them which can be used to increase the effectiveness of stents.

The principles and operation of stents and related methods according to the present invention may be better understood with reference to the drawings and the accompanying description.

Figure 1:
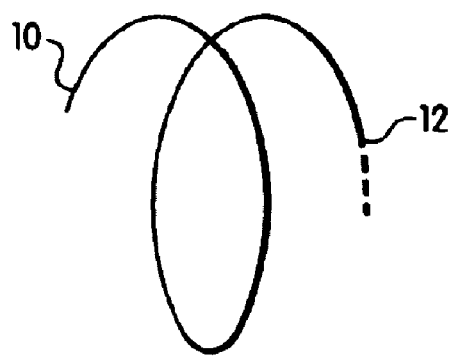
FIG. 1 is a perspective view of a single winding of a prior art stent.

Referring now to the drawing, FIG. 1 illustrates a single winding of a conventional stent. In many applications, it is important to precisely control the flexibility of the stent as well as the interloop spacing and tightness. A number of factors must be considered in selecting the proper flexibility and interloop spacing. First, the stent must be sufficiently flexible to follow the natural shape and dimensions of the body conduit into which it is installed without undue stress. The stent must also be sufficiently flexible to adequately follow the various movements of the conduit. These requirements tend to indicate that a coiled, or spring-like, structure be used.

However, the stent must not be too loose since this may erode its body conduit support function and since when the stent loosens significant interloop gaps are formed which tend to encourage the growth of surrounding tissue into the separations. Such ingrowth may have serious adverse consequences.

A stent is typically made by first tightly winding a wire of a suitable material, such as nitinol, on a mandrel. The assembly is then heated to a suitable temperature so as to impart to the stent its desired shape. However, during the heating process, the mandrel is also heated, which brings about its expansion and leads to the formation of a stent with loops which are somewhat separated from one another. Such separations are undesirable in certain applications.

Figure 2:
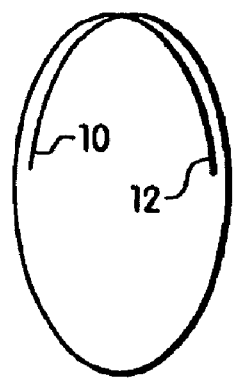
FIG. 2 is a perspective view of a single winding of stent according to the present invention which was obtained by reversing the winding of a stent such as that in FIG. 1.

These interloop gaps can be eliminated and the stent can be stiffened somewhat by reversing the winding direction of the stent after it has cooled sufficiently. Shown in FIG. 2 is the single stent winding of FIG. 1 after it has been reversed. Thus, what, prior to reversal (FIG. 1), was the left end of the loop, 10, is, after reversal (FIG. 2), the right end of the loop, 10, while what, prior to reversal (FIG. 1), was the right end of the loop, 12, is, after reversal (FIG. 2), the left end of the loop, 12. As will be appreciated, the reversal puts each loop in elastic deformation and thereby causes adjoining loops to press together and eliminates interloop gaps.

Under certain conditions a stent made by reversing the winding direction as described above may be overly rigid for a specific application. In such a case, the rigidity of the stent may be reduced to any desired level by following a reheating procedure described below.

The reversed stent 20, whose rigidity is to be reduced, is mounted onto a mandrel 22 (FIG. 3) which may or may not be the mandrel previously used to give the stent its original shape. Stent 20 and mandrel 22 are reheated at a suitable temperature above the transition point but the reheating is allowed to continue only long enough to allow the outside portion of the stent (indicated in FIG. 3 as the unhatched portion) to approach the reheating temperature and therefore to relax, while the portion of the stent near the relatively cool mandrel (indicated in FIG. 3 by hatch marks) stays at significantly lower temperatures, does not relax, and continues to have its original rigidity. In this way the reheated stent, upon cooling, displays a flexibility which is intermediate between those of the unreheated stent and a stent which is completely relaxed, but without opening up gaps between the stent loops.

The duration of the reheating must be carefully controlled to achieve the proper degree of relaxation. The reheating time will be influenced to a large degree by the heat properties of the mandrel. A mandrel which has high heat sink capacity, such as the left-hand portion of the mandrel of FIG. 3, can absorb considerable heat and keep the stent at low temperatures for a relatively long time.

Figure 3:
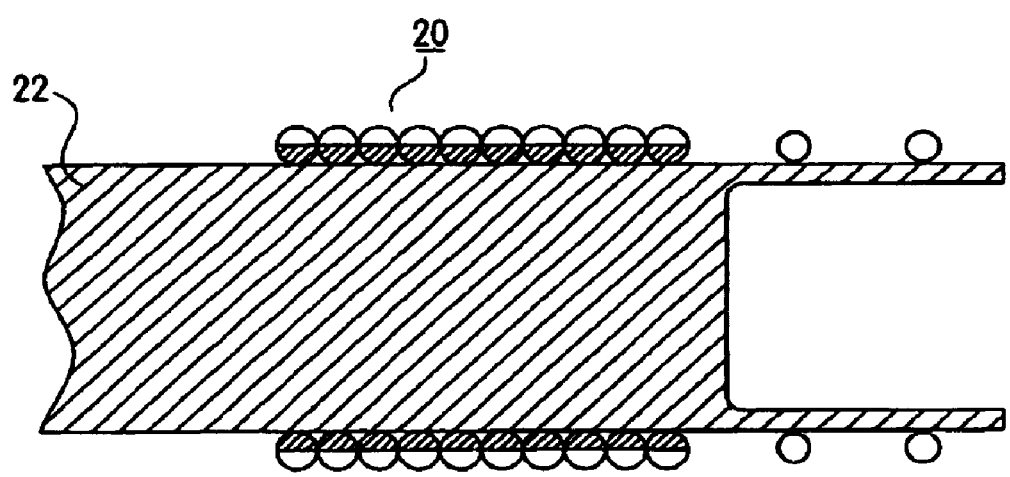
FIG. 3 is a side cross sectional view of a stent undergoing reheating according to the present invention, on a mandrel having two sections, each with a different heat sink capacity.

By contrast, a mandrel which has low heat sink capacity, such as the right-hand portion of the mandrel of FIG. 3, can absorb very little heat and will not keep the stent at low temperatures but rather will allow that portion of the stent overlying it to quickly reach the overall heating temperature and undergo complete relaxation.

Advantage may be taken of this property to reheat different portions of a stent to different extents so as to achieve a final product which has a certain rigidity in one or more sections and is relaxed and features significant interloop gaps in other sections. Typically, it may be useful to have significant interloop gaps between the windings near each end of the stent to facilitate the suturing of the stent in place.

It will be appreciated that a stent having regions of differing relaxation characteristics can also be achieved by heating the different segments to different temperatures and times, such as by use of a segmented heater or furnace.

Figure 4:
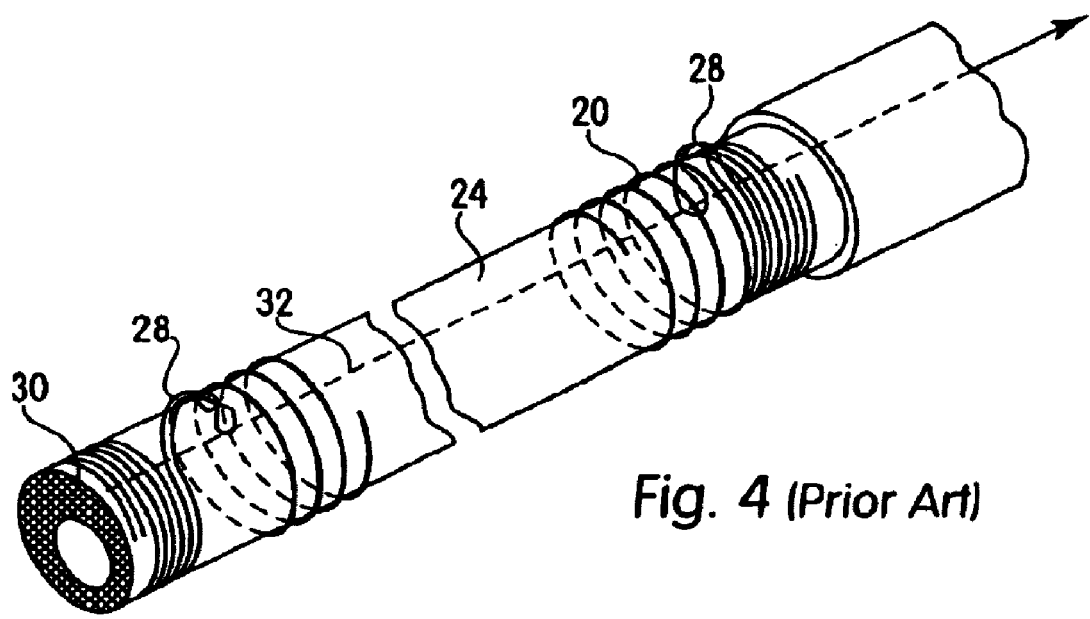
FIG. 4 is a perspective view of a stent wound and immobilized on a catheter, according to the prior art.
Figure 5:
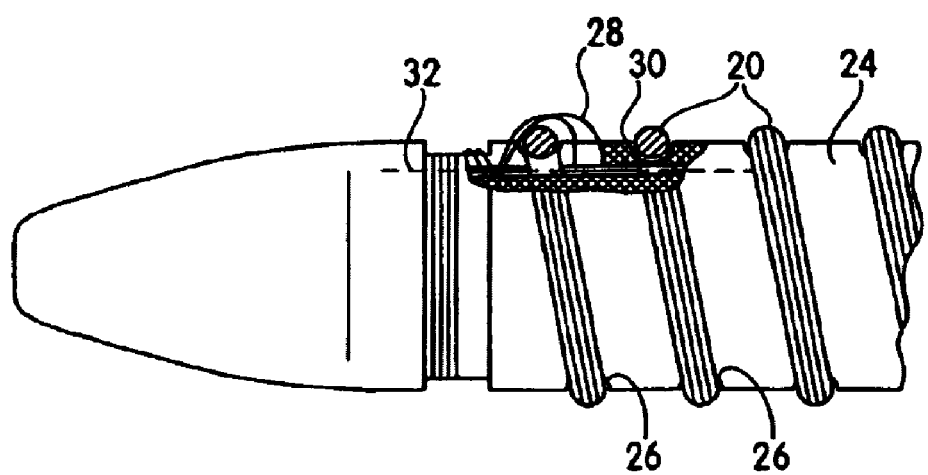
FIG. 5 is a close-up side cross sectional view of a portion of the system of FIG. 4.

Conventional stents, as well as the reversed stents according to the present invention described above, must be accurately placed in a specific location in the body conduit in order to be most effective. A common placement technique currently used is illustrated in FIGS. 4 and 5. Stent 20 is tightly wound around a catheter 24, which typically features helical grooves 26 sized and shaped to accommodate stent 20 in its tightly wound configuration.

The two ends of stent 20 are typically bulbed, i.e., the ends feature a slightly enlarged diameter. Each end of stent 20 is immobilized by a thread 28 which is anchored by wrapping around catheter 24 several times. Thread 28 is wrapped over the end of stent 20 as shown in FIG. 5. Catheter 24 features a small diameter bore 30 through which runs a release wire 32. Portions of thread 28 enter transversely into bore 30 near the bulbed end of stent 20 and thread is connected with release wire 32 (see FIG. 5) so that as long as release wire 32 is in place thread 28 immobilizes the end of stent 20. When both ends of stent 20 are so immobilized, stent 20 is effectively prevented from unwinding and resuming its preset shape.

To deploy stent 20 in the body, catheter 24 is first brought to the appropriate position. Release wire 32 is then pulled, thereby releasing the ends of stent 20. Stent 20 then immediately proceeds to unwind, enlarge and install itself into the body tubular conduit while getting shorter in proportion to the diameter growth, as is the case for a stent having adjoining loops which contact each other. However, in the process of unwinding, stent 20 assumes a final position which is somewhat arbitrary, within its original length, and which depends, to some extent, on the local resistance encountered to the unwinding in the uneven blood vessel. The lack of certainty in the accurate placement of the stent often degrades its effectiveness. Hence, it is quite important to be able to release the stent with a high degree of accuracy.

Furthermore, the unwinding action of a stent of conventional design is accompanied by the rapid turning through many cycles of the stent coils. Such a turning could have a detrimental effect on surrounding tissue since the rapid and prolonged turning could abrade or otherwise damage the interior walls of body vessels in which the stent is released.

Figure 6:
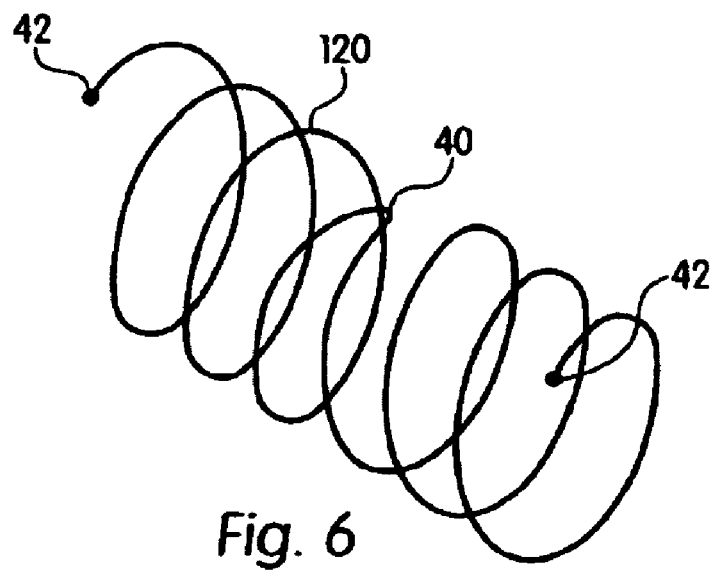
FIG. 6 is a perspective view of one embodiment of a stent according to the present invention showing two oppositely wound sections.
Figure 8:
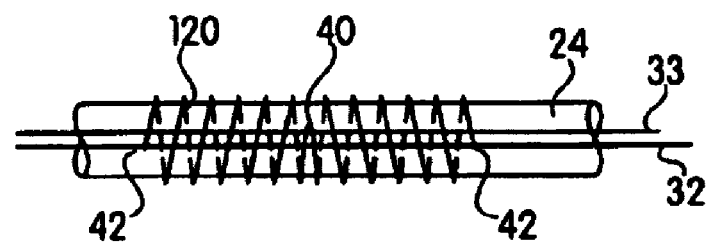
FIG. 8 is a schematic side view of the stent of FIG. 6 when wound tightly on a catheter on which the stent is delivered to its desired location.
Figure 7:
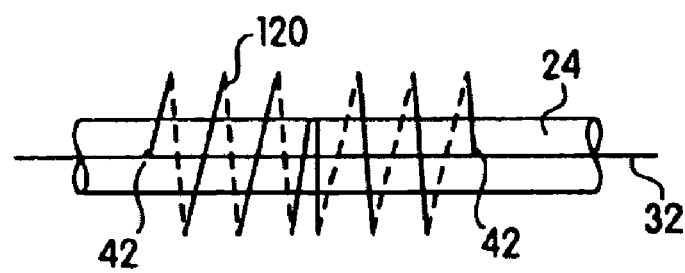
FIG. 7 is a schematic side view of the stent of FIG. 6 with reference to a catheter on which the stent is delivered to its desired location after release of the intermediate point.
Figure 9:
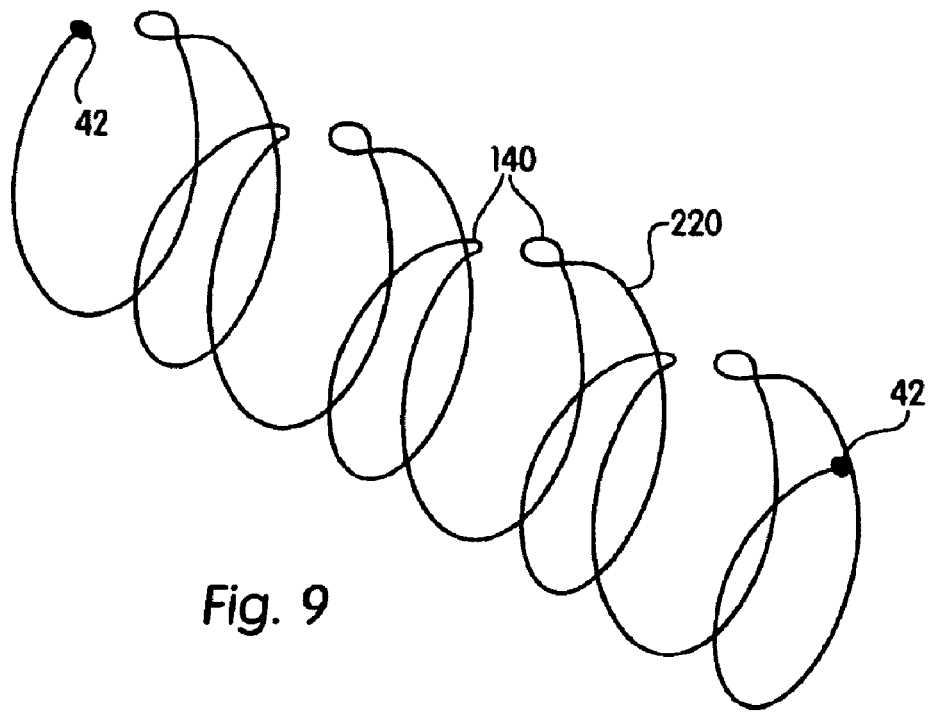
FIG. 9 is a perspective view of another embodiment of a stent according to the present invention showing a plurality of oppositely wound sections.
Figure 10:
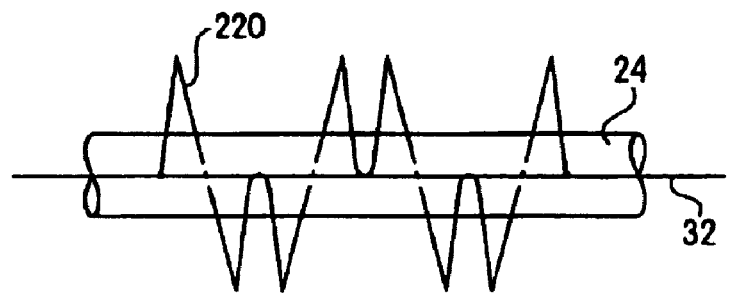
FIG. 10 is a schematic side view of the stent of FIG. 9 with reference to a catheter on which the stent is delivered to its desired location with the stent partly released.
Figure 11:
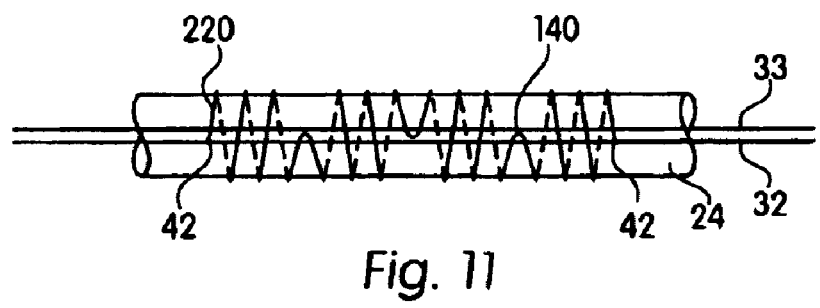
FIG. 11 is a schematic side view of the stent of FIG. 9 when wound tightly on a catheter on which the stent is delivered to its desired location.

Accordingly, a stent according to one embodiment of the present invention is made up of a coiled wire which is characterized in that the wire includes at least one section which is wound in one sense and at least one section which is wound in the opposite sense. Preferably, the stent includes two sections with each of these sections representing substantially one half of the stent. An example of such a stent is shown in FIGS. 6–8.

Stent 120 has a central point 40 where the winding direction changes, and two end points 42. To place stent 120 in a body conduit, stent 120 is first tightly wound onto catheter 24 and end points 42 are immobilized using release wire 32 as described above in the context of FIGS. 4 and 5, or in any other suitable manner. In addition, central point 40 is also immobilized in a similar manner, but using a second release wire 33.

To place stent 120, catheter 24 is first brought to the proper location. Next, central point 40 is released by using second release wire 33. This allows stent 120 to unwind without any axial displacement, since the two ends 42 are still immobilized. As stent 120 unwinds it assumes its full diameter and is firmly installed onto the inner walls of the body tubular conduit.

At this point the two end points 42 are released by using release wire 32, freeing stent 120 from catheter 24, and allowing the latter to be withdrawn. Since stent 120 is already fully unwound and firmly implanted in the body conduit prior to the release of end points 42, stent 120 does not move upon the release of end points 42 and remains firmly installed in the correct position. Shown in FIGS. 8A, 8B and 8C are more detailed views of catheter 24 and stent 120 as they might appear in an actual application.

In another embodiment of stents according to the present invention showing in FIGS. 9–12, stent 220 is made up of several sections with adjoining sections wound in opposite directions. Preferably, adjoining loops of stent 220 are wound in opposite directions, with intermediate points 140 representing the regions where winding directions change. To make such a stent, a catheter can be used which features a series of suitably placed pins or protrusions. The wire is wound about the mandrel and use is made of the pins or protrusions to wrap the wire around these in order to reverse the winding direction.

Figure 12:
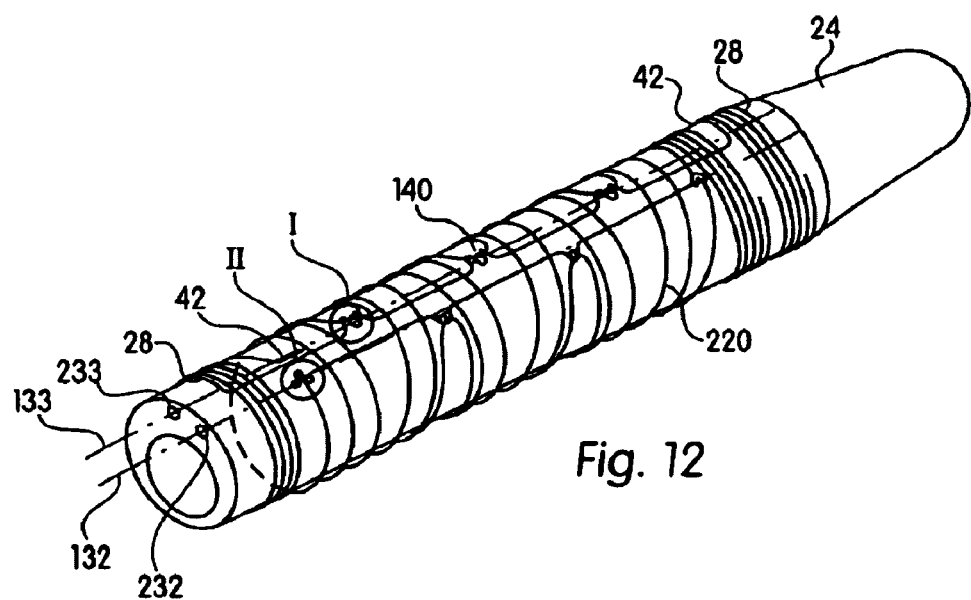
FIG. 12 is a perspective view of the embodiment of FIGS. 9–11 showing one method of immobilizing the stent.

Shown in FIG. 12 is one scheme for attaching stent 220 to catheter 24. Here a first release wire 132 immobilizes the two end points 42 and approximately one half of intermediate points 140, while a second release wire 133 serves to immobilize the balance of intermediate points 140. Each of release wires 132 and 133 is preferably located in its own bore, 232 and 233, respectively. The release of such a stent is not accompanied by the rapid and prolonged turning of the coils of the stent but is, rather, achieved by minimum and uniform turning of the coils through approximately two turns before the stent is fully deployed in the body vessel.

Figure 13:
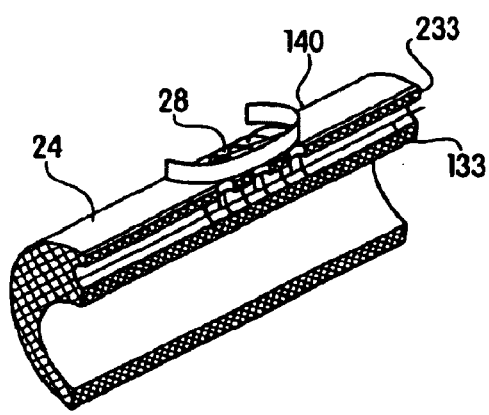
FIG. 13 is a close-up perspective cross sectional view of one portion of the system of FIG. 12 showing a tie-down of an intermediate point.
Figure 14:
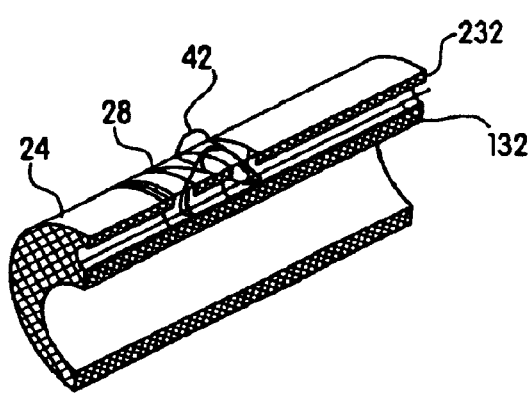
FIG. 14 is a close-up perspective cross sectional view of one portion of the system of FIG. 12 showing a tie-down of an end point.

FIGS. 13 and 14 depict possibilities for the actual immobilization of an intermediate point 140 and an end point 42, respectively.

Figure 15:
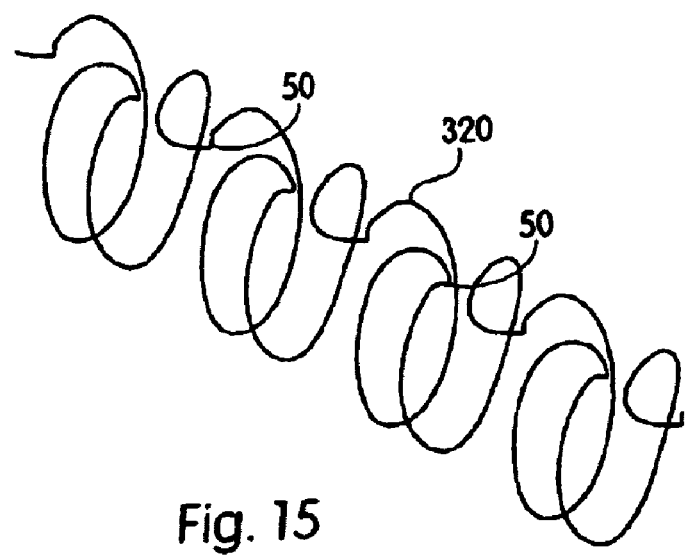
FIG. 15 is a perspective view of a variation of the embodiment of FIG. 9, showing a stent wherein the immobilization is effected in somewhat different fashion.

Another embodiment of a stent according to the present invention is shown in FIG. 15, where at the end points and in the vicinity of each winding direction change, stent 320 features a kink or depression 50 in the otherwise circular cross section of the stent. The kink or depression 50 allows stent 320 to be immobilized on a catheter (not shown) by inserting a release wire (not shown) above kink or depression 50 (see FIG. 15).

Figure 15A:
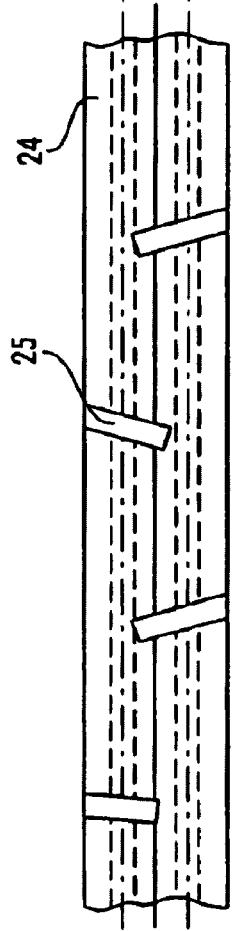
FIG. 15A is a side view of a catheter such as might be used in FIG. 15.
Figure 15B:
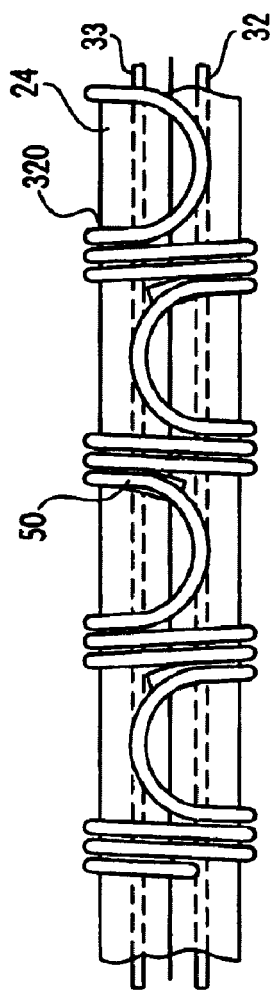
FIG. 15B is a side view of the catheter of FIG. 15A with the stent wound on the catheter.
Figure 15C:
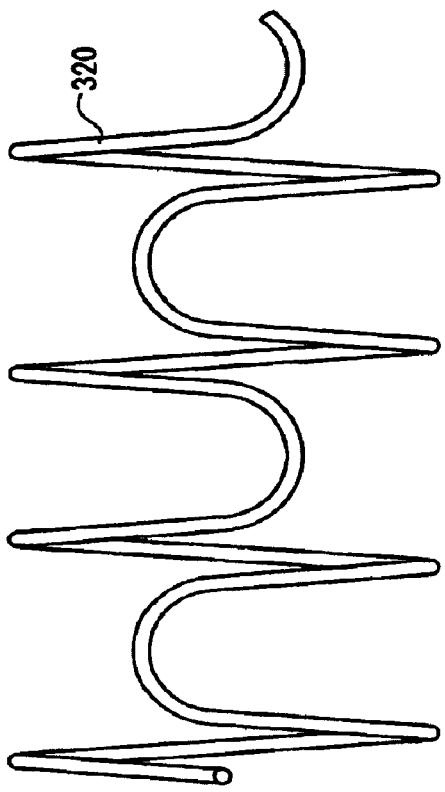
FIG. 15C is a side view of the expanded stent as it would appear after it has been released from the catheter.

As can be better seen in FIGS. 15A and 15B, catheter 24 preferably features slots 25 which accommodate the kinked portions of stent 320 so that release wires 32 and 33 can pass on the outside of the kinked portions and serve to immobilizes stent 320. FIG. 15C shows stent 320 as it would appear after release from catheter 24.

Other variations and improvements of methods of immobilizing and releasing stents, whether conventional, or those according to the present invention, may be envisioned.

When a stent is to be inserted deep into the body, the catheter used in deploying the stent is necessarily very long and may need to follow a highly convoluted path on its way to the desired deployment location. If the stent is to be released from the catheter by pulling on the release wire, the friction between the release wire and its bore may be sufficiently high that pulling the release wire will result in the deformation of the entire catheter and bring about the displacement of the catheter tip on which the stent is wound. This, in turn, could result in the improper placement of the stent.

Figure 23:
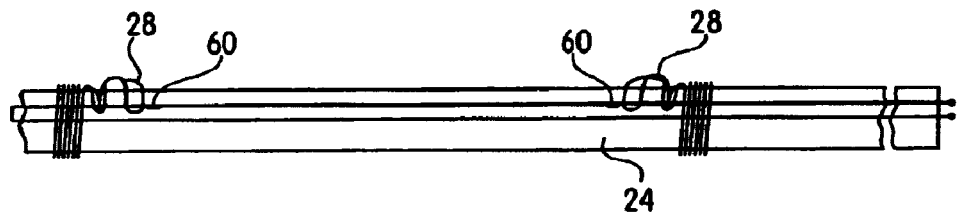
FIG. 23 is a schematic cross sectional side view of a catheter showing one embodiment of a technique for releasing the stent (not shown) using a single electrical circuit.
Figure 24:
FIG. 24 is as in FIG. 21 except that two electrical circuits are used to provide for the sequential release of various points of the stent.

One way of avoiding this difficulty is demonstrated in FIGS. 23 and 24. Here the release wire is an electrically conducting wire which, unlike the release wires described above, is not movable but is, rather, used to conduct a small electric current upon activation by the operator. In FIG. 23, a pair of threads 28 are shown, each of which is used to immobilize a certain point on the stent (not shown). Thread 28 is in contact with a heat producing element 60 which forms a part of the electrical circuit. Heat producing element 60 may be a resistor which converts electrical energy into heat. Thread 28 is made of a material such that when heat producing element 60 is activated, thread 28 is caused to melt thereby releasing the stent.

In the embodiment of FIG. 24 catheter 24 features two circuits, rather than one. This makes it possible to sequentially release various points of the stent, for example, as described above. As will readily be appreciated, the basic concept can be used in a variety of related ways. For example, thread 28 can be caused to break or disconnect by cutting, by chemical reaction, and the like.

Nitinols of certain composition have transition temperatures ranges which are such that the nitinol is in its martensite phase, and is plastic, at temperatures of about 30° C. and is in its austenite phase, and highly elastic, at or above body temperatures, above about 37° C. Such alloys are useful since stents made from them can be tightly wound about a catheter at room temperature and can then automatically resume their desired shape at normal body temperature without the need to artificially heat the stent.

However, this technique suffers from a disadvantage in that the stent may heat to body temperature prematurely, that is, before it is placed in its intended position, and may thus suffer undesirable stresses and permanent deformation. It is, thus, useful to employ nitinols which have a transition temperature range above body temperature (about 37° C.) such that the stent must be heated to a temperature above body temperature in order to convert the nitinol into its austenite phase.

In such cases conventional techniques call for the heating of stent through the circulation of hot liquids through the catheter used to place the stent. A difficulty with such techniques is that a liquid must be injected having a temperature which is sufficiently high so as to reach the stent at a temperature which is sufficiently high to raise the stent temperature above the required TTR. Especially where a long catheter must be used to reach remote body vessels, the injected liquid temperature may be high enough to cause damage to blood and other body tissues.

The problem is compounded by uncertainty as to when the heating should be discontinued, since it is difficult to know precisely when the nitinol reaches the desired temperature. As a result, there is a tendency to overheat the stent, which further incurs the risk of overheating and damaging body tissues.

To overcome these shortcomings, it is proposed that the stent be heated electrically and that advantage be taken of the differences in the properties of nitinols in their martensite and austenite phases to sense the change of phase of the nitinol to automatically regulate the heating.

Figure 25:
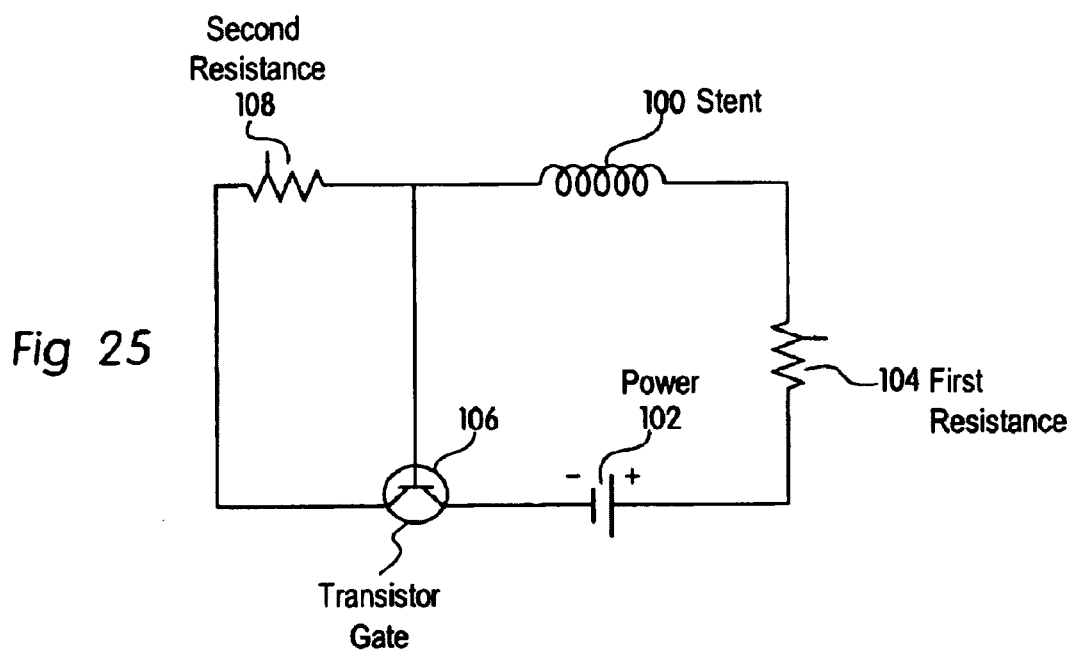
FIG. 25 is a circuit diagram for the electrical heating and phase shift sensing of a stent according to the present invention, for the automatic disconnection of the heating circuit upon, or at an appropriate time following, the detection of the phase shift.

Depicted in FIG. 25 is a circuit diagram of a stent heating and monitoring system according to the present invention. The principles and operation of such a system may be better understood with respect to a specific example described next. It is to be understood that the example is illustrative only and does not, in any way, limit the scope of the invention.

It is known that both the resistivity and the thermal conductivity of a nitinol alloy in its austenite phase are different than in its martensite phase. For example, for a particular nitinol, the resistivities are 70 and 100 µohm·cm for the martensite and austenite phases, respectively. The thermal conductivities for the same nitinol are 0.085 and 0.18 Watt/cm·C° for the martensite and austenite phases, respectively In a system according to the present invention, stent 100 would be electrically connected to a power source 102, such as a 12V battery. An appropriate first resistance 104, for example 0.018 ohm, and a second resistance 108, for example 0.036 ohm, are provided to put a desirable voltage drop in the martensite phase, say 7.5V, across stent 100, having resistance of 0.09 ohm (0.5 mm diameter and 100 mm length).

When stent 100 shifts into its austenite phase its resistance will increase to 0.13 ohm and the voltage drop across stent 100 will increase to 9V. The sharp change in voltage is an excellent indication that stent 100 has shifted into its austenite phase and can be used to control the end of the heating process, either cutting off heating immediately upon detecting the voltage change or at a certain fixed or calculated time thereafter.

For example, as shown in FIG. 25, the circuit can further include a transistor gate 106 with a threshold of 2.5V. As long as stent 100 is in its martensite phase the potential on transistor gate 106 will be 3V which is above the threshold so that the circuit will be closed. As soon as the austenite phase is reached the potential on transistor gate 106 drops to 2V, below its threshold, causing the circuit to open and the heating to be discontinued. The circuit may further have means (not shown) to continue heating beyond this point for a suitable time and at a suitable rate. It should be appreciated that a similar system can be used wherein the current drawn, rather than the voltage drop, is sensed and used to indicate the phase transition.

Figure 16:
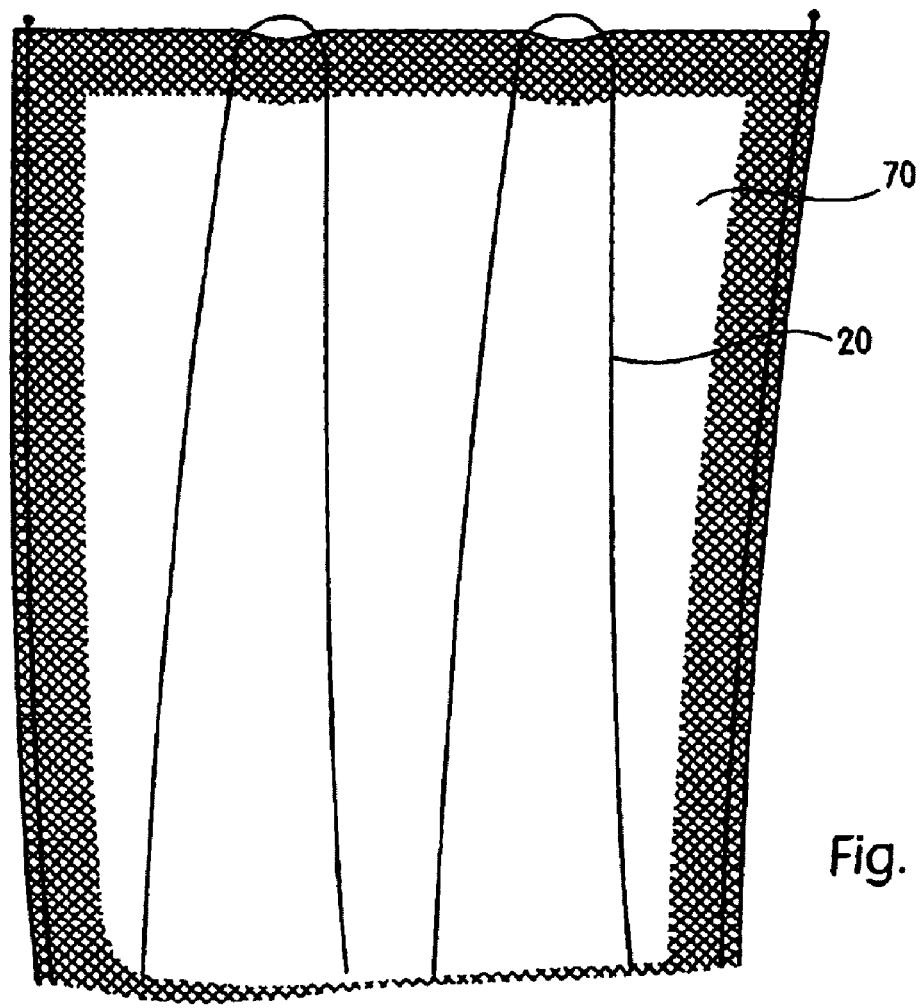
FIG. 16 is a laid-flat view of an embodiment according to the present invention wherein the stent coils are encased by a film of flexible material.
Figure 17:
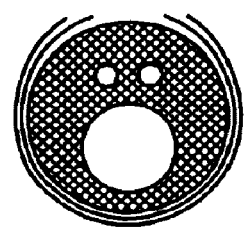
FIG. 17 is an end cross sectional view of the stent of FIG. 16 when tightly wound onto a catheter.
Figure 18:
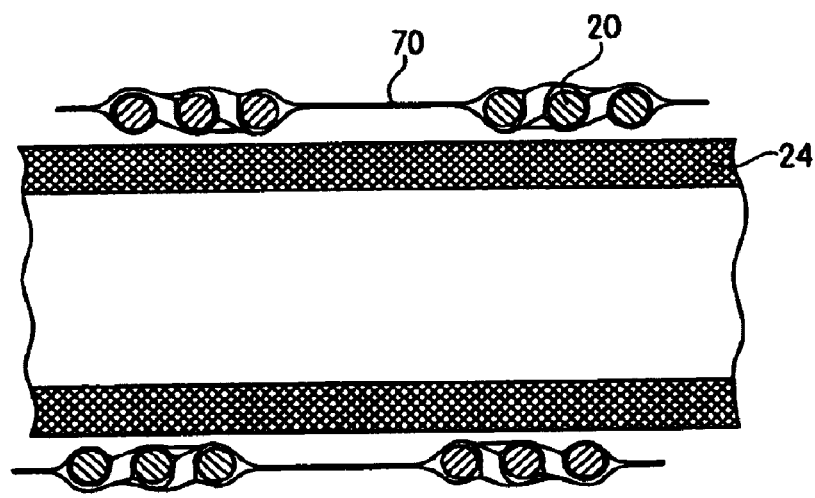
FIG. 18 is a side cross sectional view of the stent of FIG. 16 when tightly wound onto a catheter.

In some cases it is desirable that the stent form a continuous wall. This may be accomplished by encasing the wire making up the stent in a thin plastic envelop 70 (FIG. 16) which will provide the continuous wall when the stent is in position. Shown in FIGS. 17 and 18 are an end view and a side view, respectively, of stent 20 enveloped in plastic envelop 70, as it would appear when stent 20 is tightly wound on catheter 24.

Figure 16A:
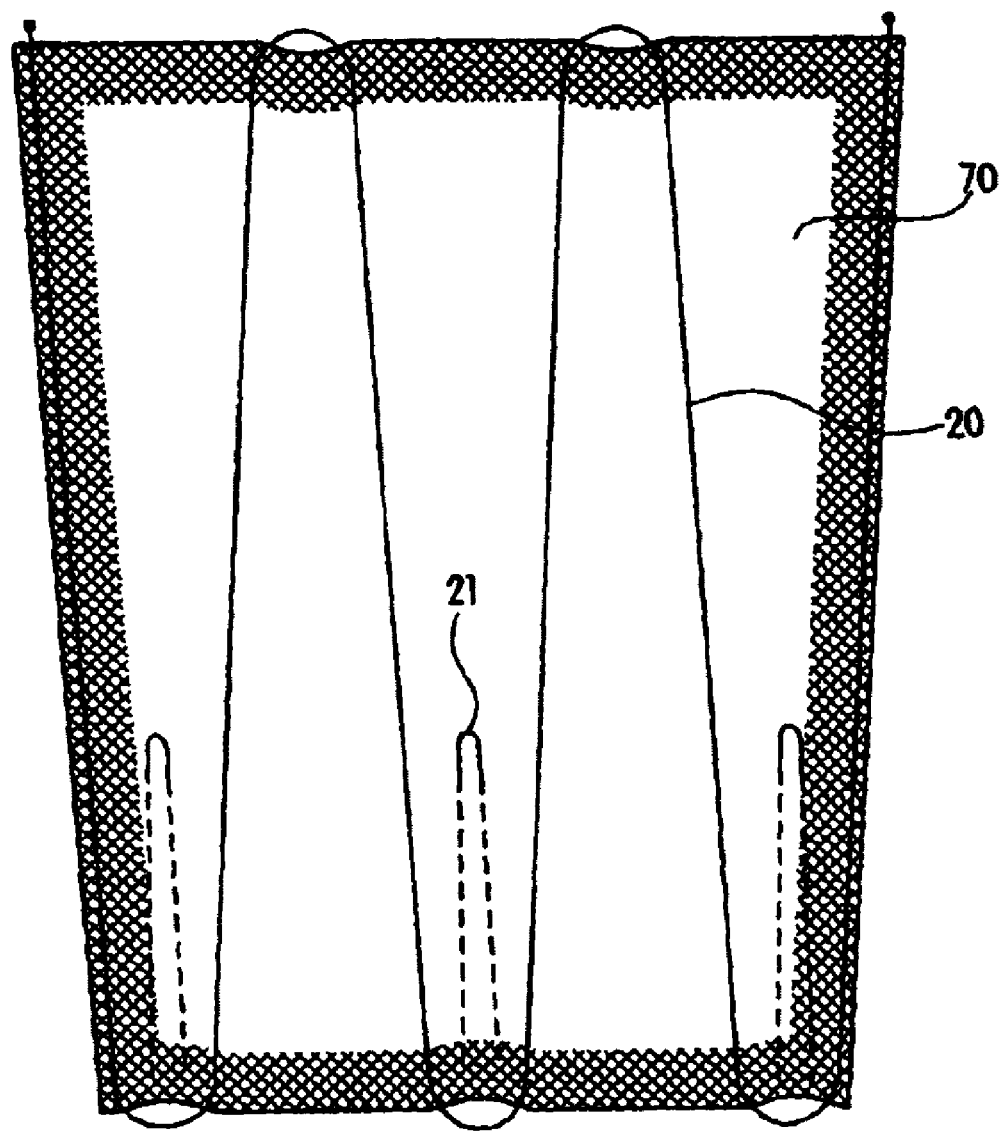
FIG. 16A is a view of another embodiment of the device of FIG. 16, including an integral immobilization thread.
Figure 16B:
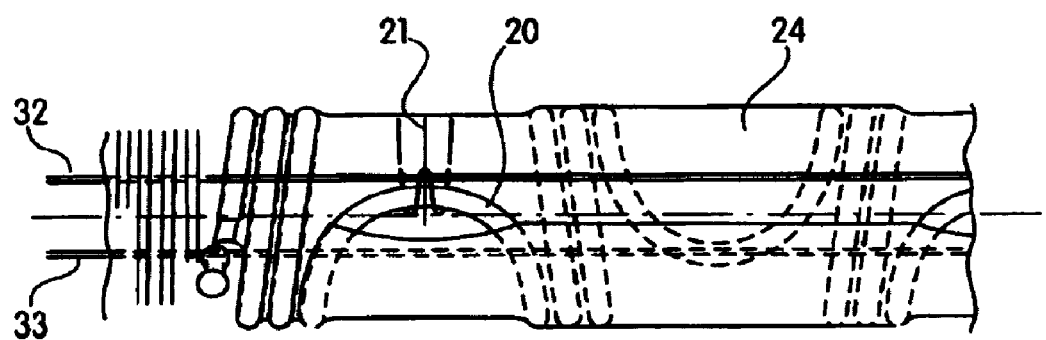
FIG. 16B is a side view of the device of FIG. 16A as it would appear when wound onto a catheter.

Another embodiment of an encased stent is shown in FIGS. 16A and 16B. The stent is as shown in FIG. 16 with the addition of a special release loops 21, preferably made of a suitable plastic material and are connected to plastic envelope 70 in some suitable fashion, which can be used (see FIG. 16B) to engage release wire 32 and immobilize the intermediate points of stent 20. The ends of stent 20 can be immobilized as described above.

Figure 19:
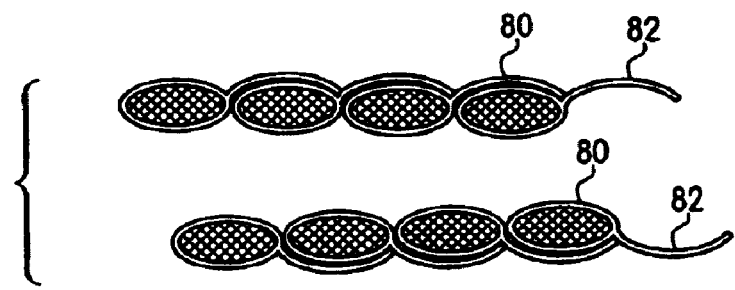
FIG. 19 is a side cross sectional view of another embodiment of a stent according to the present invention when tightly wound about a catheter (not shown)
Figure 20:
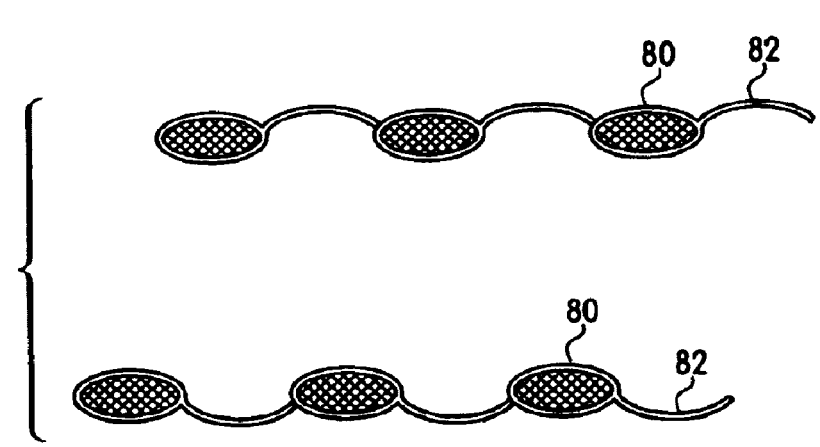
FIG. 20 is a side cross sectional view of the embodiment of FIG. 19 when unwound for deployment.

Yet another embodiment of an encased stent for effecting a continuous wall upon deployment is shown in FIGS. 19 and 20. In this embodiment a metal core 80, preferably made of nitinol, is encased in a shaped envelope 82, preferably of a suitable plastic, which allows the stent to be tightly wound on the catheter and which forms a continuous surface when the stent is unwound. Unlike the configurations of FIGS. 16–18, in the configuration of FIGS. 19 and 20, the envelope is not continuous and does not directly connect adjoining coils. Rather, the wire making up the stent is enveloped in a suitable material, such as plastic, which features an extension such that, when deployed, the extension serves to bridge the gap between adjoining coils of the stent.

The configuration shown in FIGS. 19 and 20 is such that when the stent expands and its metal core loops are separated from each other (FIG. 20) the stent retains its continuous sealed wall. Thus, a stent is obtained which features continuous walls and which is substantially the same length when wound onto the catheter for delivery and placement as when fully deployed in the body vessel. It should be noted that such a configuration may be useful even without reversing of the winding direction, since a sealed wall is maintained even when adjoining loops are not completely contiguous.

It is to be noted that a stent according to the present invention, especially one featuring a continuous wall supported on a metal coil frame, as described above, is highly desirable in that such a structure is able to support the body vessel and prevent tissue ingrowth without undue interference with the normal flow of blood and other bodily fluids. The latter characteristic is achieved through use of very thin coils and thin connecting walls enveloping the stent coils.

In addition, the profile and configuration of the stent can be adjusted so as to further minimize the flow friction of fluids flowing inside the stent and reduce turbulence. For example, the distal ends of the stent can be made to have large coil diameters than the rest of the coils so that, when the stent is deployed, its two ends press firmly against the body vessel thereby creating entrance regions for flow through the stent wherein the stent is essentially flush with the body vessel, so that drag and turbulence are minimized. It is known that turbulence, especially in blood vessels in and near the heart, is directly linked to thrombus formation.

Figure 21:
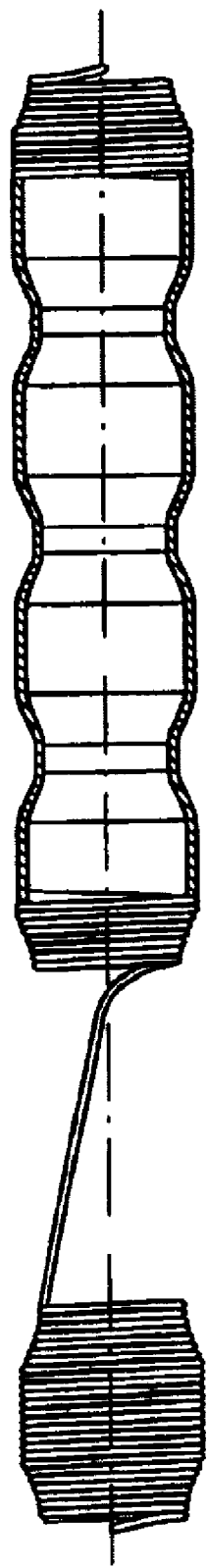
FIG. 21 is a side view of stent featuring neck-down regions and two sections connected by a coil of low pitch.
Figure 22:
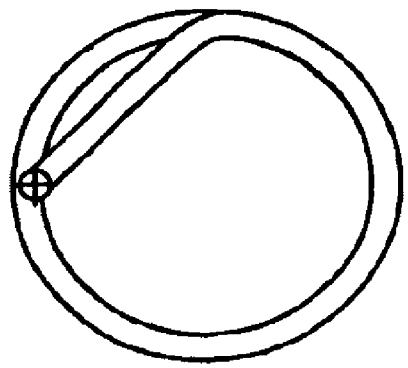
FIG. 22 is an end cross-sectional view of the stent of FIG. 21.

In certain applications it may be desirable for the stent to feature uneven contour to help anchor it in place. An example is shown in FIG. 21, where depressions are placed along the coil to increase the friction between the coil and the tissue. Furthermore, in some cases it may be advantageous to have a stent which is made up of two sections which are connected to each other by a substantially straight portion of wire, preferably connecting points on the opposing loops of the two sections which are not corresponding points, so that the wire does not unduly press against the wall of the body vessel where there is a natural constriction in the body vessel between the two sections of the stent. Preferably the connecting wire is disposed near the periphery of the stent, as shown in the end cross-sectional view of FIG. 22, to minimize the obstruction to flow of fluids through the central portions of the stent.

While the invention has been described with respect to a limited number of embodiments, it will be appreciated that many variations, modifications and other applications of the invention may be made. For example, the profile of the plastic envelope which makes up the stent can be varied so as to better conform with the internal shape of the body vessel wherein it is installed.

What is claimed is:

1. An arrangement for controlling a shape of a stent body comprising an electrical circuit for establishing an electrical current flow through the stent for heating the stent to cause the stent to shift from a martensite phase to an austenite phase thereby changing the shape of the stent body, the electrical circuit further being adapted to monitor a phase change of the stent from the martensite phase to the austenite phase and to control the flow of electrical current through the stent as a function of the phase change of the stent from the martensite phase to the austenite phase.

2. The arrangement of claim 1, wherein the electrical circuit includes a device for sensing a change in voltage across the stent to indicate the phase change.

3. The arrangement of claim 2, wherein the electrical circuit further includes a device for cutting off the supply of electrical current to the stent immediately upon sensing the change in voltage.

4. The arrangement of claim 2, wherein the electrical circuit further includes a device for cutting off the supply of electrical current to the stent a predetermined time interval after sensing the change in voltage.

5. The arrangement of claim 1, wherein the electrical circuit includes a device for sensing a change in current through the stent to indicate the phase change.

6. The arrangement of claim 5, wherein the electrical circuit further includes a device for cutting off the supply of electrical current to the stent immediately upon sensing the change in current.

7. The arrangement of claim 5, wherein the electrical circuit further includes a device for cutting off the supply of electrical current to the stent a predetermined time interval after sensing the change in current.

8. The arrangement of claim 1, wherein the electrical circuit comprises at least one resistance therein selected as a function of a resistivity of the stent.

9. The arrangement of claim 1, wherein the electrical circuit comprises at least one resistance therein selected as a function of a thermal conductance of the stent.

10. The arrangement of claim 1, wherein the electrical circuit is adapted to monitor the phase change of the stent in accordance with an abrupt change of at least one of (a) a resistivity of the stent and (b) a thermal conductivity of the stent.

11. The arrangement of claim 1, wherein the stent is formed of a shape memory material.

12. The arrangement of claim 1, wherein the stent is formed of nitinol.

13. An arrangement for controlling a shape of a stent body, comprising:
an electrical circuit adapted to establish an electrical current flow through the stent to heating the stent to cause the stent to shift from a martensite phase to an austenite phase to thereby change the shape of the stent body, the electrical circuit further adapted to monitor a phase change of the stent from the martensite phase to the austenite phase and to control the flow of electrical current through the stent as a function of the phase change of the stent from the martensite phase to the austenite phase.

14. A system, comprising:
a stent; and
an arrangement configured to control a shape of a stent body of the stent, the arrangement including an electrical circuit adapted to establish an electrical current flow through the stent to heating the stent to cause the stent to shift from an martensite phase to an austenite phase to thereby change the shape of the stent body, the electrical circuit further adapted to monitor a phase change of the stent and to control the flow of electrical current through the stent as a function of the monitor of the phase change of the stent.

15. The system of claim 14, wherein the electrical circuit includes a device adapted to sense a change in voltage across the stent to indicate the phase change.

16. The system of claim 15, wherein the electrical circuit includes a device configured to cut off the supply of electrical current to the stent immediately upon sense of the change in voltage.

17. The system of claim 15, wherein the electrical circuit includes a device adapted to cut off the supply of electrical current to the stent a predetermined time interval after a sense of the change in voltage.

18. The system of claim 14, wherein the electrical circuit includes a device adapted to sense a change in current through the stent to indicate the phase change.

19. The system of claim 18, wherein the electrical circuit includes a device configured to cut off the supply of electrical current to the stent immediately upon a sense of the change in current.

20. The system of claim 18, wherein the electrical circuit includes a device adapted to cut off the supply of electrical current to the stent a predetermined time interval after a sense of the change in current.

21. The system of claim 14, wherein the electrical circuit includes at least one resistance selected as a function of a resistivity of the stent.

22. The system of claim 14, wherein the electrical circuit includes at least one resistance selected as a function of a thermal conductance of the stent.

23. The system of claim 14, wherein the electrical circuit is adapted to monitor the phase change of the stent in accordance with an abrupt change of at least one of (a) a resistivity of the stent and (b) a thermal conductivity of the stent.

24. The system of claim 14, wherein the stent is formed of a shape memory material.

25. The system of claim 14, wherein the stent is formed of nitinol.

* * * * *